United States Patent
Patel (10) Patent No.: US 11,326,144 B2
(45) Date of Patent: May 10, 2022

(54) PARTICULATE LYOPHILIZED PLATELET LYSATE COMPOSITIONS

(71) Applicant: Amit Patel, Miami, FL (US)

(72) Inventor: Amit Patel, Miami, FL (US)

(73) Assignee: Powder Life LLC, Shalimar, FL (US)

( * ) Notice: Subject to any disclaimer, the term of this patent is extended or adjusted under 35 U.S.C. 154(b) by 335 days.

(21) Appl. No.: 15/577,888

(22) PCT Filed: May 31, 2016

(86) PCT No.: PCT/US2016/035100
§ 371 (c)(1),
(2) Date: Nov. 29, 2017

(87) PCT Pub. No.: WO2016/196515
PCT Pub. Date: Dec. 8, 2016

(65) Prior Publication Data
US 2018/0163172 A1  Jun. 14, 2018

Related U.S. Application Data (60) Provisional application No. 62/168,516, filed on May 29, 2015.

(51) Int. Cl.
| | |
|---|---|
| C12N 5/00 | (2006.01) |
| C12N 5/0735 | (2010.01) |
| C12N 5/0797 | (2010.01) |
| C12N 5/074 | (2010.01) |
| A61K 9/19 | (2006.01) |
| A61K 35/19 | (2015.01) |

(52) U.S. Cl.
CPC .............. *C12N 5/0018* (2013.01); *A61K 9/19* (2013.01); *A61K 35/19* (2013.01); *C12N 5/0606* (2013.01); *C12N 5/0623* (2013.01); *C12N 5/0696* (2013.01); *A61L 2300/252* (2013.01); *A61L 2300/412* (2013.01); *C12N 2500/84* (2013.01); *C12N 2502/115* (2013.01); *C12N 2506/03* (2013.01); *C12N 2506/1369* (2013.01); *C12N 2506/45* (2013.01); *C12N 2533/50* (2013.01)

(58) Field of Classification Search
CPC .............. C12N 5/0018; C12N 2500/84; C12N 2502/115; A61K 35/19; A61K 9/19; A61L 2300/252; A61L 2300/412
See application file for complete search history.

(56) References Cited

U.S. PATENT DOCUMENTS

| | | | |
|---|---|---|---|
| 5,834,418 A | 11/1998 | Brazeau et al. | |
| 2005/0143684 A1 | 6/2005 | Bolan et al. | |
| 2005/0191286 A1 | 9/2005 | Gandy | |
| 2006/0051731 A1 | 3/2006 | Ho et al. | |
| 2006/0142198 A1 | 6/2006 | Gandy | |
| 2009/0023211 A1 | 1/2009 | Persson et al. | |
| 2011/0123503 A1 | 5/2011 | Rebulla et al. | |
| 2011/0171731 A1 | 7/2011 | Dietz et al. | |
| 2011/0200642 A1 | 8/2011 | Centeno | |
| 2011/0280952 A1 | 11/2011 | Caramella et al. | |
| 2012/0156306 A1 | 6/2012 | Weissman et al. | |
| 2012/0276632 A1 | 11/2012 | Strunk et al. | |
| 2013/0195959 A1* | 8/2013 | Patel | A61K 35/19 424/447 |
| 2014/0127314 A1 | 5/2014 | Copland et al. | |
| 2015/0064133 A1 | 3/2015 | Woods et al. | |

FOREIGN PATENT DOCUMENTS

| | | |
|---|---|---|
| EP | 2540819 | 1/2013 |
| WO | WO 2013/113024 A1 | 8/2013 |

OTHER PUBLICATIONS

Declaration of Amit Patel under 37 C.F.R. § 1.132 dated Jun. 9, 2015 published in IFW of U.S. Appl. No. 13/358,797 (Year: 2015).*
Fekete et al., Platelet lysate from whole blood-derived pooled platelet concentrates for the isolation and expansion of human bone marrow mesenchymal stromal cells: production process, content and identification of active components. Cytotherapy, vol. 14, No. 5 (May 2012) pp. 540-554. (Year: 2012).*
Sartopore Capsule 0.2µm. Datasheet [online]. Sartorius Stedim Biotec, 2020 <URL:https://www.sartorius.com/shop/us/en/usd/bioprocess-products-and-services-filtration-and-purification-technologies-sterile-filtration-process-economy/sartopore%C2%AE-capsule-0-2%C2%B5m/p/5441307H5--OO--B >. (Year: 2020).*
Alemany et al.; "In Vitro Evaluation of the Hemostatic Effectriveness of Non Viable Platelet Preparations: Studies With Frozen-Thawed, Sonicated or lyophilized Platelets." Vox Sanguinis, vol. 73 (1997) pp. 36-42.
Brinkhous et al., "Preservation of Platelet Receptors for Platelet Aggregating Factor/Von Willebrand Factor by Air Drying, Freezing, or Lyophilization" New Stable Platelet Preparations for Von Willebrand FactorAssays. Thrombosis Research, vol. 13 (1978) pp. 591-597.
Crespo-Diaz et al, "Platelet Laysate Consisting of a Natural Repair Proteome Supports Human Mesenchymal Stem Cell Proliferation and Chromosomal Stability", Cell Transplantation, 2011, pp. 797-811, vol. 20, Cognizant Comm. Corp.
Gawaz et al. "Platelets in Inflammation and Atherogenesis." Journal of Clinical Investigation, vol. 115 No. 12 ; Dec. 1, 2005; pp. 3378-3384.

(Continued)

*Primary Examiner* — Kara D Johnson
(74) *Attorney, Agent, or Firm* — Thorpe North & Western, LLP (57) ABSTRACT

A particulate lyophilized platelet lysate composition suitable for use as a cell culture medium can include growth factors, cytokines, and chemokines released from lysis of source platelets, wherein cellular debris from the source platelets is removed (partially or fully) by filtration. The growth factors, cytokines, and chemokines are lyophilized to form a particulate lyophilized platelet lysate composition.

39 Claims, 4 Drawing Sheets

(56) References Cited

OTHER PUBLICATIONS

Mannello et al, "Concise Review: No Breakthroughs for Human Mesenchymal and Embryonic Stem Cell Culture: Conditioned Medium, Feeder Layer, or Feeder-Free; Medium with Fetal Calf Serum, Human Serum, or Enriched Plasma; Serum-Free, Serum Replacement Nonconditioned Medium, or Ad Hoc Formula? All That Glitters Is Not Gold!", Stem Cells, 2007, pp. 1603-1609, vol. 25.
O'Shaughnessey et al., Blood-Derived Anti-Inflammatory Protein Solution Blocks the Effect of Il-1β.
PCT/US2013/023490; filed Jan. 28, 2013; Jadi Cell LLC; international search report dated Jun. 24, 2013.
PCT Application No. PCT/US16/35100, Filing Date May 31, 2016, Amit Patel, International Search Report, dated Nov. 3, 2016; 13 Pages.
Ranzato et al, "Platelet Lysate Modulates MMP-2 and MMP-9 Expression, Matrix Deposition and Cell-To-Matrix Adhesion in Keratinocytes and Fibroblasts", Experimental Dermatology, Oct. 2010, pp. 7, John Wiley & Sons A/S.
Roesken et al., Acceleration of Wound Healing by Topical Drug Delivery via Liposomes. Langenbeck's Archives of Surgery, vol. 385; 2000; pp. 42-49.
Search Report for European application 13740649.2 dated Aug. 7, 2015, 9 pages.
Woodell-May et al., Autologous Protein Solution Inhibits MMP-13 Production by IL-1β on.
Human Articular Chondrocytes. Journal of Orthopedic Research, vol. 29, No. 9 (Sep. 2011) pp. 1320-1326.
Wolkers et al., "Human Platelets Loaded With Trehalose Surive Freeze-Drying." Cryobiology, vol. 42 (2001) pp. 79-87.
Mojica-Henshaw et al.; "Serum-Converted Platelet Lysate can Substitute for Fetal Bovine Serum in Human Mesenchymal Stromal Cell Cultures;" Cytotherapy; (2013); pp. 1458-1468; vol. 15; <doi: 10.1016/j.jcyt.2013.06.014 >.
Tzu-Bi Shih et al.; "Preparation, Quality Criteria, and Properties of Human Blood Platelet Lysate Supplements for Ex Vivo Stem Cell Expansion;" New Biotechnology; (Jan. 2015); pp. 199-211; vol. 32, No. 1; <doi: 10.1016/j.nbt.2014.06.001 >.
Extended European Search Report dated Oct. 18, 2018, in EP Application No. 16804259.6, filed May 31, 2016, 8 pages.
Patil et al.; "Pulmonary Drug Delivery Strategies: A Concise, Systematic Review;" Lung India; (Jan.-Mar. 2012); pp. 44-49; vol. 29, No. 1; <doi: 10.4103/0970-2113.92361 >.
Ranzato et al.; "Platelet Lysate Stimulates Wound Repair of HaCaT Keratinocytes;" British Journal of Dermatology; (Sep. 1, 2008); pp. 537-545; vol. 159, No. 3; <doi: 10.1111/j.13652133.2008.08699.x.

\* cited by examiner

PARTICULATE LYOPHILIZED PLATELET LYSATE COMPOSITIONS

The present application is a National Stage of International Application No. PCT/US2016/035100, filed on May 31, 2016, which claims the benefit of U.S. Provisional Patent Application No. 62/168,516, filed on May 29, 2015, each of which is incorporated herein by reference in its entirety.

BACKGROUND

Cell therapy and cellular research are increasing in mainstream medicine. As a result of the increase, a variety of culture mediums have been created. Fetal bovine serum (FBS) based culture medium is one of the more common types, can be manufactured on a large scale, reducing lot to lot variability, and can be used when culturing human cells. However, cell cultures created on FBS based culture medium can be exposed to immunogenic residual bovine proteins creating purity concerns. One alternative culturing medium can be created from human platelet lysates. Human platelet lysates based culture mediums can outperform and eliminate exposure concerns associated with cell cultures plated on FBS based culture mediums; however, these mediums have stringent storage conditions. Therefore, a cell culture medium that eliminates the exposure concerns associated with FBS based culture mediums and can be easily stored is in demand.

BRIEF DESCRIPTION OF THE DRAWINGS

Features and advantages of the technology will be apparent from the detailed description that follows, taken in conjunction with the accompanying drawings, to illustrate features of the technology. It is understood that these figures merely depict exemplary embodiments and are not, therefore, to be considered limiting in scope. Furthermore, it will be readily appreciated that the components, as generally described and illustrated in the figures herein and elsewhere, could be formulated and/or designed in a wide variety of different manners.

These figures are provided to illustrate various aspects of the technology and are not intended to be limiting in terms of results or components unless otherwise limited by the claims.

DETAILED DESCRIPTION

Reference will now be made to exemplary embodiments and specific language will be used herein to describe the same. It will nevertheless be understood that no limitation of the scope of the invention is thereby intended. Alterations and further modifications of the inventive features illustrated herein, and additional applications of the principles of the disclosure as illustrated herein, which would occur to one skilled in the relevant art and having possession of this disclosure, are to be considered within the scope of the invention. It is also to be understood that this disclosure is not limited to the particular configurations, process steps and materials disclosed herein, as these may vary to some degree. Further, it is to be understood that the terminology used herein is used for the purpose of describing particular embodiments only, and is not intended to be limiting as the scope of the present disclosure.

It is noted that, as used in this specification and the appended claims, singular forms of "a," "an," and "the" include plural referents unless the content clearly dictates otherwise.

As used herein, the term "platelet-containing fluid" refers to any fluid, either biological or artificial, which contains platelets. Non-limiting examples of such fluids include various forms of whole blood, blood plasma, platelet rich plasma, concentrated platelets in any medium, or the like, derived from human and non-human sources.

As used herein, the term "concentrate" or "concentrating" refers to the separation of platelets from the bulk of the plasma, whole blood, or other fluid from which it is present. For example, centrifugation, spectrometry, filtration, decanting, gravity settling, or other methods of concentrating platelets from platelet-containing fluids can be used. When concentrating platelets, it can be desirable to use an anticoagulant (particularly for centrifugation or gravity settling) along with the source of platelets to prevent clotting during the separation of platelets from other components of the blood, plasma, or other fluid.

The term "anticoagulant" refers to compositions that inhibit clotting when concentrating or collecting platelets for use in accordance with examples of the present disclosure. Anticoagulants generally are available as inhibitors of clotting factor synthesis, inhibitors of thrombin, or antiplatelet drugs. Inhibitors of clotting factor synthesis that inhibit the production of certain clotting factors in the liver, include compositions such as warfarin (Coumadin). Inhibitors of thrombin interfere with blood clotting by blocking the activity of thrombin, and include compositions such as heparin and lepirudin (Refludan). Antiplatelet drugs interact with platelets themselves, and include drugs such as aspirin, ticlopidine (Ticlid), clopidogrel (Plavix), tirofiban (Aggrastat), eptifibatide (Integrilin), etc.

The terms "lyophilization," lyophilize," or the like refer to a freeze-drying or dehydration process that is often used to preserve platelets, but is used somewhat differently in accordance with embodiments of the present disclosure. Specifically, lyophilization is used primarily not just as a preservative process, but can further be used to further lyse platelets after initial freeze-thaw or other lysis technique is conducted. In other words, in accordance with examples of the present disclosure, after lysates are formed as described herein, lyophilization provides the added benefit of preserving the growth factors, cytokines, chemokines, and other contents initially enclosed within or bound to the surface the platelets, but which are released when platelets are lysed as described herein, e.g., freeze-thaw lysing. The process typically works by freezing the material and reducing surrounding pressure to allow frozen water in the material to sublimate directly from the solid phase to the gas phase. Lyophilization can likewise be carried out after lysing cells using techniques other freeze-thaw cycling, including sonication and/or filtering, or any combination of these lysis techniques.

The term "tissue" includes the full range of small tissue sites to complete organs.

In accordance with the present disclosure, a "lysate" is the composition prepared where platelets are destroyed by disrupting their cell membrane. This can be done chemically, mechanically, by liquid homogenization, filtration, and/or sonication, but in accordance with certain embodiments described herein, the cytolysis can be carried out using a freeze-thaw cycle, and to a lesser degree, as part of a final lyophilization process. Freeze-thaw lysates can be formed by freezing a platelet suspension and then thawing the material to above room temperature, e.g., 30° C. to 45° C., though other freeze-thaw regimens are also included in the scope of the present disclosure, provided they lead to cytolysis of the platelets. With the freeze-thaw technique, this method causes cells to swell and break as ice crystals form, followed by contraction at thawing. Thus, the cyclical swelling and contracting ultimately causes the platelets to break open. Multiple cycles are typically used for more complete lysis, but the "more complete" lysis is not necessarily required in accordance with examples of the present disclosure. Varying degrees of platelet cytolysis can occur, e.g., at least 30%, at least 50%, at least 70%, at least 90%, or up to 100% cytolosys, by platelet count. When lysing platelets, two or more freeze-thaw cycles, three or more cycles, etc., can be used. Alternatively, one freeze-thaw cycle can be used, followed by a lyophilization step. Thus, regardless of the technique, one or more lysing step (e.g., freeze-thaw, sonication, filtration, liquid homogenization, mechanical lysing, chemical lysing, etc.) is carried out followed by a lyophilization step (e.g., freeze drying or dehydration). The lyophilization step can cause additional lysing to occur over and above the one or more lysis step.

The term "lyophilized platelet lysates" or "LPL" are prepared as described herein. However, it is noted that the term lyophilized platelet lysates also includes "lyophilized platelet rich plasma lysates" or "LPRRL" as a specific type of lyophilized platelet lysates. Thus, any discussion of lyophilized platelet lysates (LPL) also includes lyophilized platelet rich plasma lysates (LPRRL), with the understanding that one difference is that platelet rich plasma is used or formed as part of the method or composition. However, in either composition, both include lyophilized platelet lysates.

When referring to a reconstituted particulate lyophilized platelet composition formulated as a cellular culture medium that "does not exhibit clotting activity," it is understood that there may either be no clotting activity, or only de minimis clotting activity that does not interfere with the growth of the cell or tissue sample in the culture medium.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of components may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. This same principle applies to ranges reciting only one numerical value. Furthermore, such an interpretation should apply regardless of the breadth of the range or the characteristics being described.

With these definitions in mind, a particulate lyophilized platelet lysate composition suitable for use as a cell culture medium can include growth factors, cytokines, and chemokines released from lysis of source platelets, wherein cellular debris from the source platelets is removed by filtration, and wherein the growth factors, cytokines, and chemokines are lyophilized to form a particulate lyophilized platelet lysate composition. In one specific example, a method of culturing cells or tissue can include reconstituting the particulate lyophilized platelet lysate composition to form a cell culture medium, and contacting cells or tissue with the cell culture medium to form cells or tissue in culture. The media can be used for cell cultures derived from mesenchymal stem cells, human embryonic stem cells, keratinocytes, or cardiomyocytes. In some embodiments, the mesenchymal stem cells can be derived from an umbilical cord. Other cell types can likewise be used.

In another example, a cell culture medium can include particulate lyophilized platelet lysates reconstituted in a liquid medium, wherein the cell culture medium is formulated at a concentration that does not exhibit clotting activity within a cell or tissue in culture. In one specific example, a method of culturing cells or tissue can include contacting cells or tissue with the cell culture medium to form cells or tissue in culture. Again, the media can be used for cell cultures derived from mesenchymal stem cells, human embryonic stem cells, keratinocytes, or cardiomyocytes. In some embodiments, the mesenchymal stem cells can be derived from an umbilical cord. Other cell types can likewise be used.

In another example, a method for preparing a lyophilized platelet lysate composition can include the steps of obtaining a platelet source including platelets and a fluid carrier; lysing the platelets to form a plurality of lysates; and filtering the plurality of lysates after lysis to remove cellular debris. In this example, an additional step can include lyophilizing the plurality of lysates to form a particulate lyophilized platelet lysate composition having released concentrations of available growth factors, cytokines, and chemokines. In one specific example, the particulate lyophilized platelet lysate composition, when reconstituted as a cell culture medium, does not cause clotting activity in a live cell or tissue culture.

As noted in the above examples, one advantage of the compositions of the present disclosure is that these compositions can be prepared so that they do not exhibit or promote clotting in cell or tissue cultures, i.e. no more than de minimus clotting that does not substantially negatively impact the cell or tissue culture. In some examples, an amount of at least 50 wt %, or from about 10 wt %, 20 wt %, or 30 wt % to about 50 wt %, 60 wt %, or 70 wt % lyophilized platelet lysates in the cell culture medium does not exhibit or promote clotting. The inhibited clotting activity of the LPLs is believed to result from the degree of lysis. Varying degrees of platelet lysis can occur. In one embodiment, at least 15% of the source platelets that remain in the composition by platelet count are lysed to form the lyophilized platelet lysates. In another embodiment, at least 30% of the source platelets that remain in the composition by platelet count are lysed to form the lyophilized platelet lysates. In yet another embodiment, at least about 50% of the source platelets that remain in the composition by platelet count are lysed to form the lyophilized platelet lysates. In one example, at least 70% of the source platelets that remain in the composition by platelet count are lysed to form the lyophilized platelet lysates. In another example at least 90% of the source platelets that remain in the composition by platelet count are lysed to form the lyophilized platelet lysates. In yet another example at least 99% of the source platelets that remain in the composition by platelet count are lysed to form the lyophilized platelet lysates.

In some embodiments, the cell culture medium does not contain any additional components outside of the solvent that the LPL particulate composition is dissolved or dispersed in when reconstituted for use as a cellular or tissue culture medium. The particulate lyophilized platelet lysate composition can be reconstituted using any liquid medium appropriate for the intended purpose of the cell culture medium. In some embodiments, the LPLs can be reconstituted in a liquid medium (such as DMEM, saline, plasma, DMSO, MEM alpha, RPMI, B-mercaptoethanol, non-essential amino acids, sodium pyruvate, glutamine, the like, or combinations thereof) at appropriate concentrations for the intended application. In some examples, the LPL particulate composition can be rehydrated at different concentrations ranging 0.01% to 100%, 1% to 90%, 10% to 80%, or 20% to 70%, by volume, and mixed with a liposome solution within its hydrophobic membrane. In other embodiments, the cell culture media can be admixed with additional components, other than the solvent. In one embodiment, the cell culture media is admixed with other culture medium product(s) that are known in the art. In yet another embodiment, the cell culture media can further comprise an active or biologic agent. The active or biologic agent can comprise at least one of an antifungal, an antiviral, an antibiotic, growth factors, and/or other chemicals specific to the media's intended use. The amount of the active or biological agent can be any concentration that meets the needs of the media's intended use. When combined with any additional components, the amount of the combined LPLs and freeze-dried growth factors, cytokines, and chemokines in the media can be present at from about 5%, 10%, 15%, 20%, 25%, 30% or 40% to about 50%, 60%, 70%, 80%, 90% or 95%, by weight. In one specific example, the amount of combined LPLs and freeze-dried growth factors, cytokines, and chemokines can be from about 20 wt % to about 90 wt %, or from about 30 wt % to about 80 wt %, or from about 40 wt % to about 70 wt %. The cell culture media can be formulated for in vivo or in vitro use.

The activity of the particulate lyophilized platelet lysate composition can be stable for extended periods of time. In one embodiment, the particulate lyophilized platelet lysate composition can be stable when stored at −80° C. for at least five years. In another embodiment, the particulate lyophilized platelet lysate composition can be stable when stored at 4° C. for at least 1 year or even longer, e.g., at least 2 years, at least 3 years, etc. In yet another embodiment, the particulate lyophilized platelet lysate composition can be stable when stored at room temperature for at least one year. In some embodiments, storing the particulate lyophilized platelet composition for at least 12 months at −80° C., 4° C., or room temperature, the composition can be readily reconstituted in a liquid medium and substantially or completely retain its properties, e.g., stem cell culture properties and function and support for cell cultures that are not substantially impacted with respect to stem cell proliferation or differentiation. In other embodiments, the particulate lyophilized platelet composition, even when stored for lengthy periods of time as outlined above, retains the ability to double the amount of plated cells within 24 hours.

The particulate lyophilized platelet composition can demonstrate the ability for continued multi-potency after one year of storage and followed by then being reconstituted. In some embodiments, the cell culture medium can be used to grow stem cells that differentiate adipogenicly, chondrogenicly, and/or osteogenicly. The ability of the cultured media to differentiate cells can occur after the particulate lyophilized platelet lysate composition (prior to reconstitution) is stored at −80° C. for at least one year, at 4° C. for at least one year, or at room temperature for at least one year. In some embodiments when mesenchymal stem cells are expanded on the cell culture media, the mesenchymal stem cells can phenotypically comprise at least one of CD166, CD73, CD29, CD9, CD13, CD71, and CD90. In some embodiments, the phenotypic analysis can result in at least 90% detection of the above mentioned proteins.

In some embodiments, in obtaining platelets, any platelet source can be used, including platelets derived from whole blood. In one embodiment, the platelet source can be platelet rich plasma. In one embodiment, the platelets can be derived from a mammalian platelet source. In yet another embodiment, the platelets can be derived from a non-human animal source. In further embodiments, the platelets can be derived from a human source. Regardless of the source, the platelets can be tested to ensure they are free of any infectious agents.

The platelets can be concentrated, if desired, using any method known in the art. For example, platelets can be concentrated from a platelet containing fluid to form a platelet rich portion. Non-limiting examples of concentrating methods can include centrifugation or commercially available platelet purification devices.

After platelet concentration, the platelets can be lysed. Lysis can occur using any method known in the art. In some embodiments, the lysis can be a result of sonication, filtration carried out in a way that causes lysis, and/or freeze-thawing.

When lysis occurs via a freeze-thaw process, the resultant concentrated platelet material, such as, in some examples, a concentrated platelet rich portion, can be frozen, such as with liquid nitrogen at about −190° C. or to at least about −80° C. using dry ice and ethanol, acetone, or the like, or other freeze assisting compositions, apparatus (e.g., a −80° C. freezer, or other suitable apparatus), or a combination thereof. A number of freezing temperatures can be used in addition to those listed above. However, in some embodiments, the freezing temperature can be about −80° C. or below. A low temperature, such as −80° C. or below, can be effective at rapidly freezing the sample, or a significant proportion of the sample, such that a large number of platelets are frozen within a few minutes. In some examples, rapid freezing can prevent the formation of large ice crystals that can damage intracellular constituents and can more effectively preserve the integrity of intracellular growth factors, cytokines, and chemokines. Thus, in some examples, it can be advantageous to expose the platelets to a sufficiently low temperature to freeze the sample, or at least a portion of the sample, as quickly as possible, such as within 5 minutes, 10 minutes, 20 minutes, 30 minutes, or 60 minutes. However, in some examples, complete freezing can take a period of hours, e.g. from about 12 hours to about 36 hours, about 24 hours to about 48 hours, or at least 12 hours, at least 24 hours, at least 36 hours, at least 48 hours, or other suitable time period. Complete freezing of the sample prior to thawing can effectively increase the amount of platelets that are lysed during a single freeze-thaw cycle. Additionally, more thorough freezing per cycle can reduce the number of freeze-thaw cycles that need to be performed to achieve adequate lysis of the platelets. Reducing the number of freeze-thaw cycles to achieve an adequate amount of desired intracellular constituents can reduce the thermal stress placed on those constituents. It is noted that the volume of the sample can affect the amount of time required to achieve a complete freezing of the sample. For example, larger volumes can require longer periods of time to achieve a complete freezing of the sample.

After freezing for a period of time, such as in one example, to achieve complete freezing of the sample, the concentrated platelet material can then be quickly thawed to above room temperature, e.g., from 30° C. to 45° C., 34° C. to 40° C., 30° C. to 35° C., 39° C. to 45° C., or in one example, at about 37° C. This freeze-thaw cycle can then be repeated to increase the concentration of platelet lysates. In some examples, a single freeze-thaw cycle of the platelets can be performed at a temperature of −80° C. or below for a period of at least 48 hours. In some examples, where additional freeze-thaw cycles are performed, each additional cycle can be performed for a period of from about 24 hours to about 48 hours.

Generally, the more cycles that are carried out, the more platelets that will be lysed. When further lysis occurs, increased amounts of growth factors, cytokines, and chemokines will be present in the resultant material. The quantity of freeze-thaw cycles can be repeated until a pre-determined degree of lysis occurs. The pre-determined degree of lysis can be at least 30%, at least 40%, at least 50%, at least 70%, or at least 90% cytolysis. In some examples, a single or first freeze-thaw cycle, with a freezing period of at least 48 hours, can lyse at least 35% or from about 35% to about 45% of platelets in a platelet source and can provide at least 60 ng of released growth factors and other cellular constituents, such as cytokines and chemokines, per ml of lysate. In some examples, two freeze-thaw cycles (where freezing period for additional cycles is from 24 hours to 48 hours) can lyse at least 55% or from about 55% to about 65% of platelets in a platelet source and can provide at least 90 ng of released growth factors and other cellular constituents, such as cytokines and chemokines, per ml of lysate. In some examples, three freeze-thaw cycles (where freezing period for additional cycles is from 24 hours to 48 hours) can lyse at least 65% or from about 65% to about 75% of platelets in a platelet source and can provide at least 140 ng of released growth factors and other cellular constituents, such as cytokines and chemokines, per ml of lysate. In some examples, four freeze-thaw cycles (where freezing period for additional cycles is from 24 hours to 48 hours) can lyse at least 75% or from about 75% to about 85% of platelets in a platelet course and can provide at least 190 ng of released growth factors and other cellular constituents, such as cytokines and chemokines, per ml of lysate. In some examples, five freeze-thaw cycles (where freezing period for additional cycles is from 24 hours to 48 hours) can lyse at least 90% or from about 90% to about 100% of platelets in a platelet source and can provide at least 230 ng of released growth factors and other cellular constituents, such as cytokines and chemokines, per ml of lysate.

In some embodiments, from one to all of the freeze-thaw cycles can be followed by filtration. In some examples, filtration can be used prior to or separately from freeze-thaw lysis. Filtering, or at least partially filtering, the plurality of lysates can partially, substantially, or fully remove cellular debris, e.g., lysed membrane and other large particles, as well as intact platelets, thereby providing a clean and concentrated platelet lysate composition. Accordingly, the resulting lysate can include a solids content of at least 50 wt %, at least 70 wt %, or at least 90 wt % growth factors, cytokines, chemokines, or a combination thereof that are released from platelets during lysis. Additionally, filtration can increase the amount of platelet lysis achieved in a given sample by from about 5% to about 15%, or more than 15%. For example, where a single freeze-thaw cycle achieved platelet lysis of about 40% of platelets in the sample, subsequent filtration of the sample can, in some examples, increase platelet lysis to from about 42% to about 46%, or more. Filtration can also decrease the amount of potential bacterial contamination in the platelet lysate.

A number of suitable filter membranes can be used. Typically, filter membranes can have low protein binding affinity and/or can be suitable for use with biological samples. In some examples, the filter membrane can be made of a material selected from the group consisting of polyvinylidine difluoride (PVDF), hydrophilic polytetrafluoroethylene (PTFE), regenerated cellulose (RC), polyethylene (PE), polycarbonate track etched (PCTE), polyester track etched (PETE), polyethersulfone (PES), asymmetric PES, cellulose acetate (CA), and combinations thereof. In some examples, the filter membrane can have a pore size of from about 0.1 microns to 0.3 microns, e.g., about 0.22 microns, about 0.2 microns, or about 0.1 microns. In some examples, the filter membrane can have a pre-filtration membrane or layer such as glass microfiber, asymmetric polyethersulfone, or other suitable pre-filter. In some examples, the platelet lysate samples can be allowed to pass through the filter via gravimetric pressure. In other examples, a vacuum or positive pressure can be applied to the platelet lysate sample to expedite the passage of the sample through the filter. Generally, filtration under positive or negative pressure can increase the amount of platelet lysis in the platelet lysate sample. The higher the positive or negative pressure introduced, the greater the increase in platelet lysis.

After the platelet lysates are filtered, they can be lyophilized or freeze-dried using standard lyophilization techniques. For example, the filtered platelet lysates can be frozen in liquid nitrogen or frozen in a dry-ice and ethanol or acetone solution. After freezing, the sample can be fluidly coupled to a freeze dryer and allowed to dry under standard lyophilization parameters to a predetermined dryness. For example, the sample can be dried to have less than 15 wt % water content, less than 10 wt % water content, less than 7 wt % water content, less than 5 wt % water content, less than 3 wt % water content, or less than 1 wt % water content. For long-term storage, it can be desirable to freeze-dry the sample until it has a water content of less than 3 wt % or less than 1 wt %. Once the platelet lysate is lyophilized it can form a particulate lyophilized platelet lysate composition. Once dried, the particulate lyophilized platelet lysate composition can include at least 50 wt %, at least 70 wt %, or at least 90 wt % growth factors, cytokines, chemokines, or a combination thereof that are released from platelets during platelet lysis. As described above, cellular debris and intact platelets can be largely removed during the filtration step so as to increase the concentration or potency of the lysates in the composition.

As mentioned, the particulate lyophilized platelet lysate composition can be reconstituted using any liquid medium appropriate for the intended purpose of the cell-cultured medium. This type of medium, enriched with LPLs, can be used for culturing mammalian cells, particularly human cells when human platelets are used for research or therapeutic applications. It should be noted that LPLs are useful for growing or deriving various types of cells or tissue, including but not limited to, mesenchymal stem cells from various tissues, human embryonic stem cells, keratinocytes, cardiomyocytes, and many other cell types within the human body, as the lyophilized platelet lysates prepared in accordance with the present disclosure contain growth factors, cytokines, and chemokines that allow for the growth of cells and tissues, as well as maintaining organs and their functions, etc.

In some examples, the culture medium can be made of different LPL samples. For example, the culture medium can be made in part of an LPL sample that was obtained using a low number of freeze-thaw cycles and in part of an LPL sample that was obtained using a high number of freeze-thaw cycles. In some examples, this can be advantageous as the number of freeze-thaw cycles can have differing effects on different cellular constituents. For example, some cellular constituents can be more prevalent under conditions that induce a lower degree of cytolysis, while other cellular constituents will be more prevalent under conditions that induce a higher degree of cytolysis, and vice versa.

In some examples, an additional culture medium can be admixed with the LPL culture medium to form a cell culture admixture medium. In some examples, the additional culture medium can include from about 10 wt % to about 90 wt %, about 20 wt % to about 80 wt %, or about 30 wt % to about 70 wt % of the cell culture admixture medium. In some examples, the cell culture admixture medium can retain the ability of the cell culture medium to double the amount of plated cells within 24 hours after the cell culture medium has been stored for at least one year at −80° C., 4° C., or room temperature.

The cell culture media can be prepared in large batches. In one embodiment, the cell culture media is prepared in a batch size of from about 0.5 L to about 1000 L, 1 L to 500 L, 10 L to 1000 L, etc. More specifically, the batch size can be each about 0.5 L, 1 L, 10 L, 100 L, 200 L, 400 L, 500 L, or 750 L. The ability to produce large batch sizes can result in cultured media with reduced lot to lot variability.

It will be readily apparent to those skilled in the art that various changes and modifications of an obvious nature may be made without departing from the spirit of the disclosed technology embodiments, and all such changes and modifications are considered to fall within the scope of the technology as recited herein, including in the appended claims. One example of such changes and modifications could include, but is not limited to, incorporating additional components in the culture medium and/or using storage temperatures in between those stated herein.

EXAMPLES

The following examples illustrate embodiments of the present disclosure that are presently best known. However, it is to be understood that the following are only exemplary or illustrative of the application of the principles of the present disclosure. Numerous modifications and alternative compositions, methods, and systems may be devised by those skilled in the art without departing from the spirit and scope of the present disclosure. The appended claims are intended to cover such modifications and arrangements. Thus, while the present disclosure has been described above with particularity, the following examples provide further detail in connection with what is presently deemed to be the most practical embodiment.

Example 1—Preparation of Particulate Lyophilized Platelet Lysate Compositions and Reconstituted Cell Culture Media Peripheral blood is collected with an appropriate amount of anticoagulant to prevent clotting of the blood during processing. In this example, 35 mL of blood is collected, which is then centrifuged at 200×g (1000 rpm) for 10 minutes at 4° C. with the brake set to off mode. After centrifugation, the platelet rich portion is removed and tubes of the platelet rich portion are placed into a freezing range of −190° C. to −80° C. for a period of 24 hours. After 24 hours, the platelets are lysed by thawing quickly at 37° C. After thawing, the tubes are then filtered and returned for another freeze cycle within the same freezing range for a period of 24 hours. The freeze-thaw cycle (one freeze cycle followed by one thaw cycle) is repeated at least one additional time, and more typically, repeated at least twice for a total 3 cycles, e.g., 3 to 6 freeze-thaw cycles. Following one or more of the freeze-thaw cycles, the lysed platelets can be filtered to remove cellular membrane and debris. It is notable that sonication, filtration, or the like, can be used to lyse or collect platelets as well, either alternatively or additively with respect to the freeze-thaw cycle described herein. After the last freeze-thaw cycle, the tubes are refrozen at −80° C. and stored overnight. The following day, the tubes are lyophilized using FreeZone 2.5 Plus (Labconco) under 0.008 mBar at −84° C. for 48 hrs. The lyophiliziation can further lyse additional platelets as well. Depending on the total volume to be lyophilized, the time may be increased beyond the 48 hours. Likewise, in some embodiments, the time may be decreased to some degree. A particulate lyophilized platelet lysate composition is formed. The composition can then be reconstituted in a liquid medium, stirred, heated, and poured into a petri dish or test tube.

Example 2—Mesenchymal Stem Cell Study

Particulate lyophilized platelet lysate compositions prepared similarly as described in Example 1 were each stored for 3, 6, 9, and 12 months at −80° C., 4° C., and room temperature. Reconstituted lyophilized platelet lysate composition after these storage periods were compared in function with a commercially prepared medium XcytePLUS™ (available from iBiologics™, LLC, Arizona, and stored only at −80° C.) based on flow cytometry, cell morphology, doubling rates, and differentiation potential on umbilical cord derived mesenchymal stem cells. It should be noted that XcytePLUS™ cannot be stored for long periods of time at 4° C. or at room temperature.

Flow Cytometry

Phenotypic analysis of mesenchymal stem cells expanded in all human platelet lysate conditions were tested using flow cytometry. 90% positive results or greater were identified for CD166, CD73, CD29, CD9, CD13, CD71, and CD90 in all cultured mediums stored at the various conditions described above. Little to no positive results were indicated for CD106, HLA-DR -DP -DQ, CD86, CD137, CD133/2, and Stro1.

Morphology

Inverted light microscopy was utilized to evaluate the mesenchymal stem cell morphology for cells expanded in all human protein lysate conditions. All of the cultured mediums stored at the various conditions described resulted in stable morphology.

Growth Curve

Figure 1:
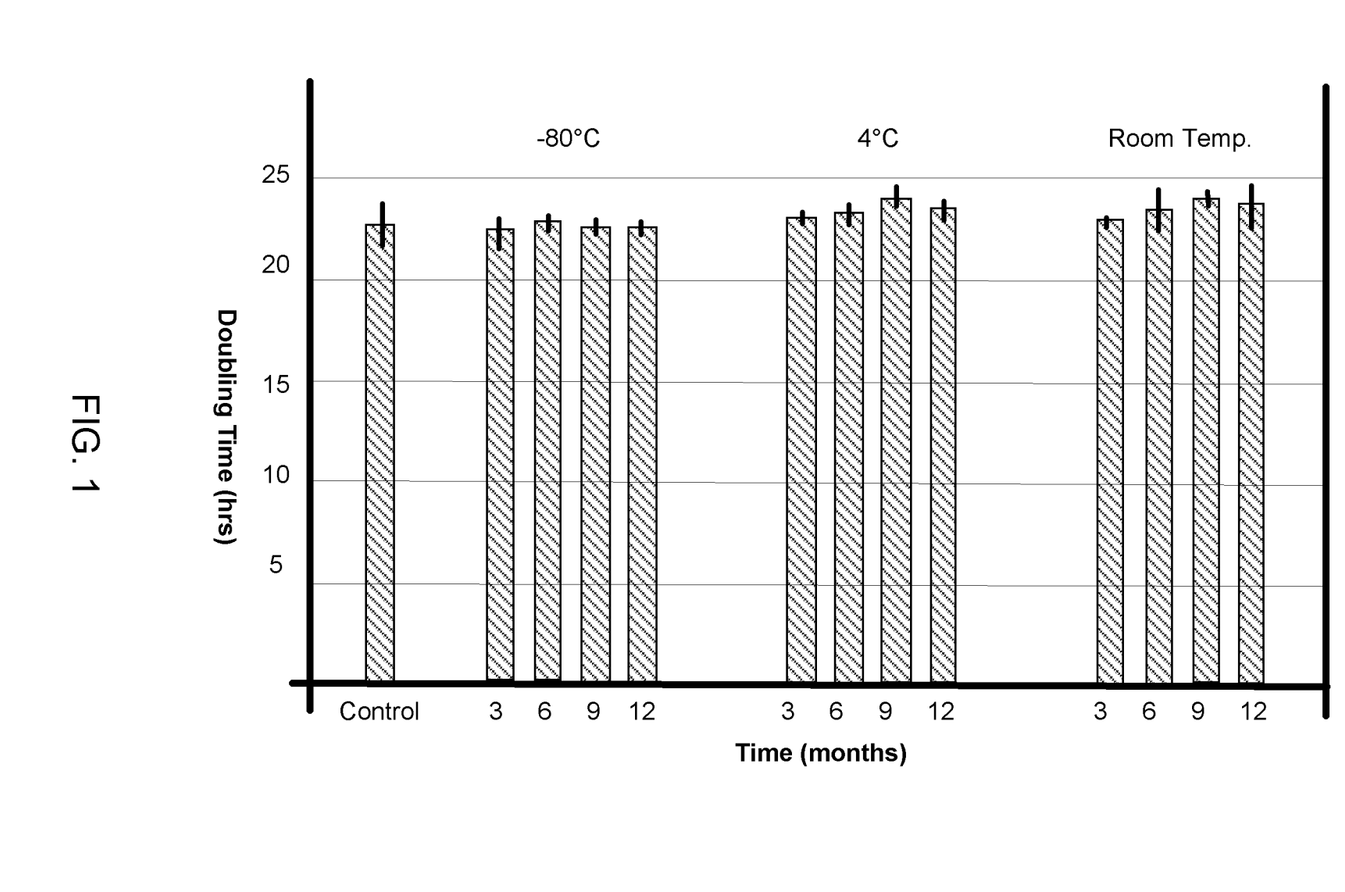
FIG. 1 schematically shows the growth curve results for cryopreserved passage three umbilical cord derived mesenchymal stem cells in human platelet lysate cultured media following storage at a variety of temperatures and time periods.

Cryopreserved passage 3 umbilical cord derived mesenchymal stem cells were plated at 2100 cells/cm$^2$ in media supplemented with 10% human platelet lysates. The cells were harvested at 80-90% confluence and re-plated for two more passages. The doubling time of mesenchymal stem cells grown for each condition was statistically calculated. All of the cultured media stored at the various conditions and storage periods resulted in doubling at time periods between 20-25 hours. The results of the growth curve testing are shown on FIG. 1.

Differentiation Potential

Figure 2:
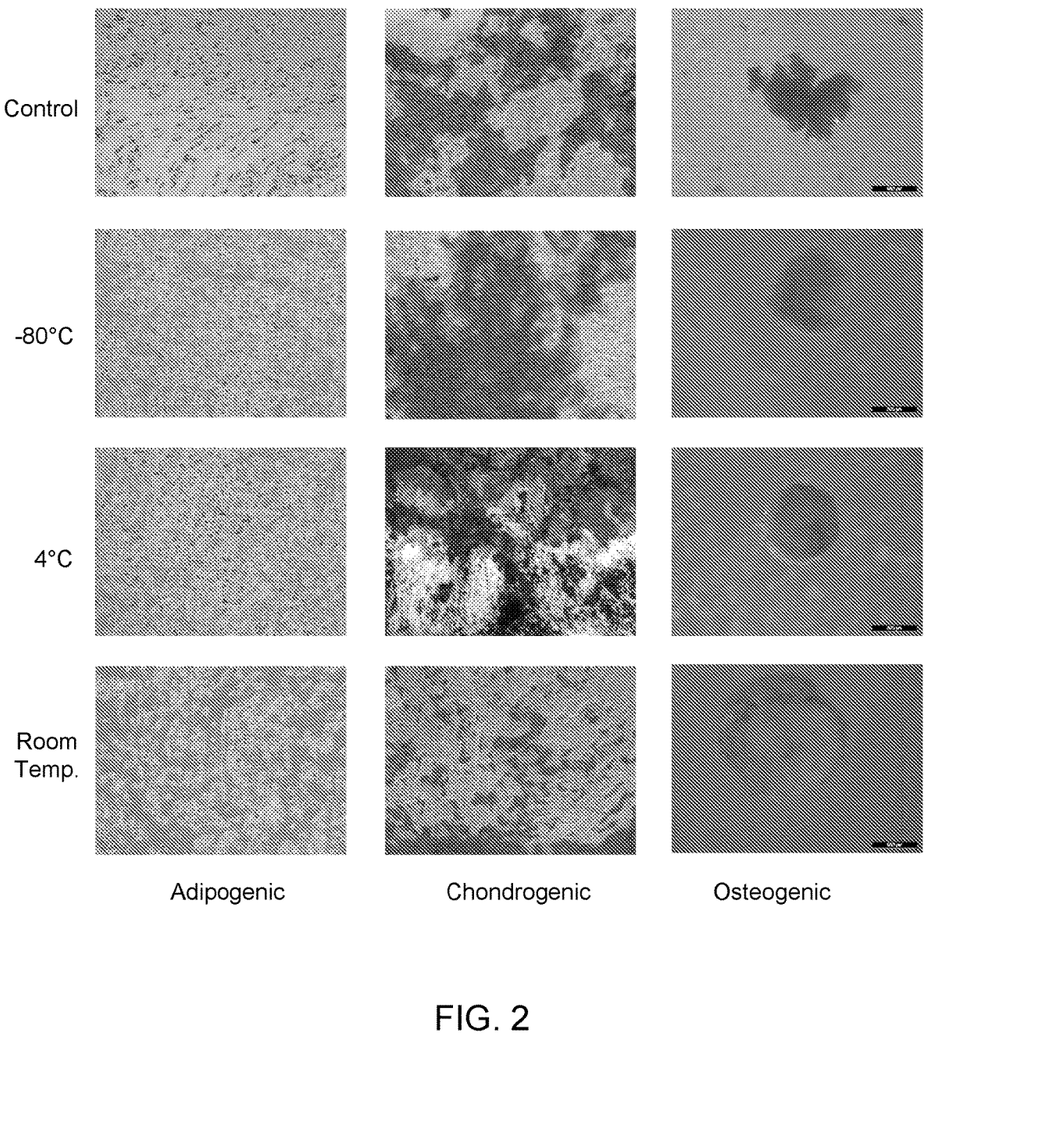
FIG. 2 schematically shows black and white images of cell differentiation for cryopreserved passage three umbilical cord derived mesenchymal stem cells plated in human platelet lysate cultured media including a control medium and experimental media stored at a variety of temperatures for a period of 12 months.

The multi-potency of the mesenchymal stem cells expanded in the human platelet conditions were tested for adipogenic, chondrogenic, and osteogenic differentiation. The results indicate that all of the cultured media stored at the various conditions and storage periods as described above resulted in cell differentiation. FIG. 2 displays images of the differentiation taken using differentiation kits (from Life Technologies, Grand Island, N.Y.).

Example 3—Platelet Lysis Study

Figure 3:
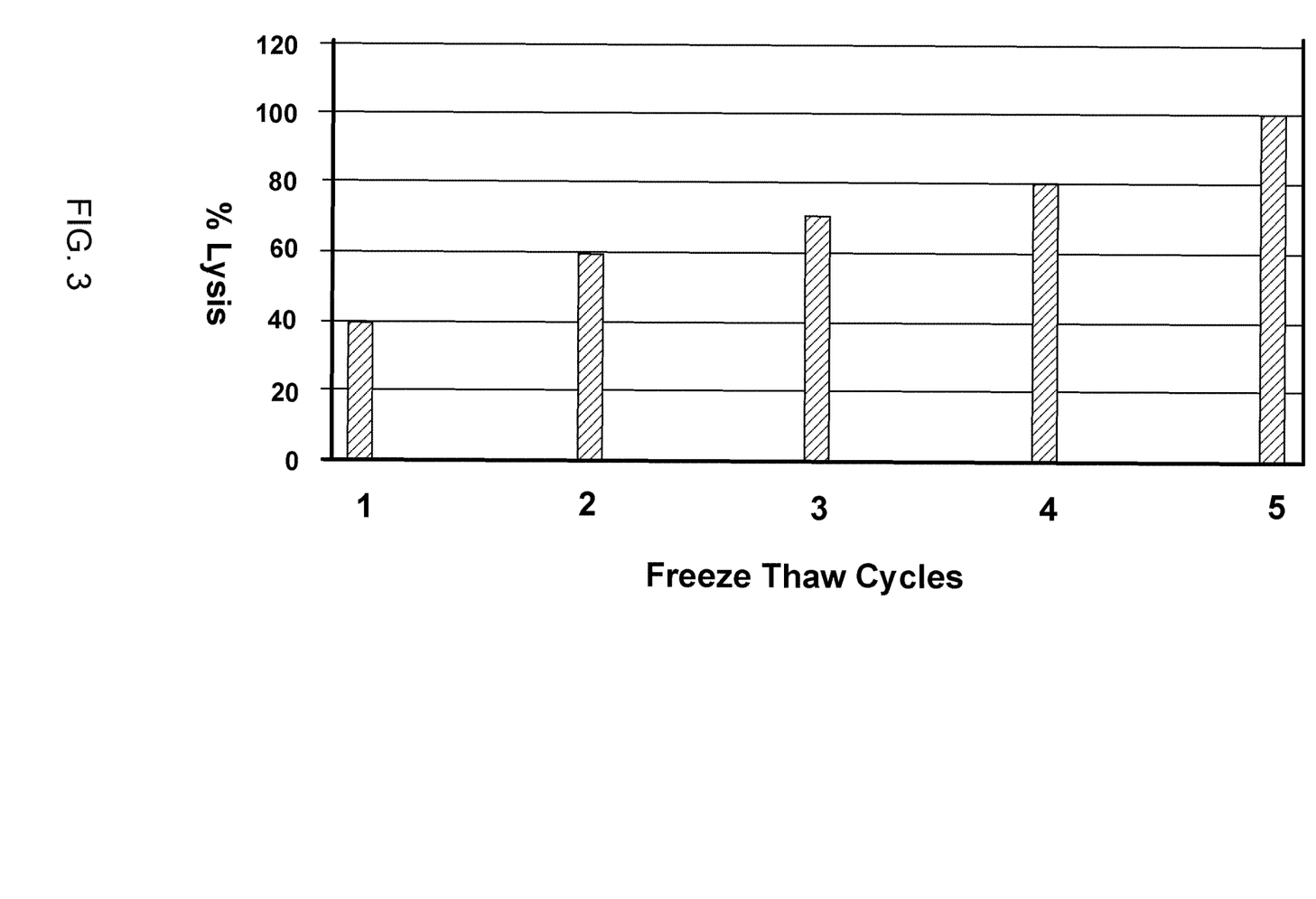
FIG. 3 schematically shows the percentage of platelets lysed per freeze-thaw cycle of a freeze-thaw lysis method for one group of samples.

Platelet rich samples were obtained in the same manner as described in Example 1. The platelet rich samples are placed into a freezing range of −190° C. to −80° C. for a period of 48 hours. After 48 hours, the platelets are lysed by thawing quickly at 37° C. A first set of samples was assayed to determine the amount of lysed cells after a single freeze-thaw cycle. Additional samples were re-frozen for a period of from 24 hours to 48 hours and re-thawed as described above for a total of two, three, four, and five cycles, respectively. The results of this study are depicted in FIG. 3. As can be seen in FIG. 3. Complete lysis of all platelets was achieved with 5 freeze-thaw cycles. In contrast, a single freeze-thaw cycle achieved only about 40% lysis.

Figure 4:
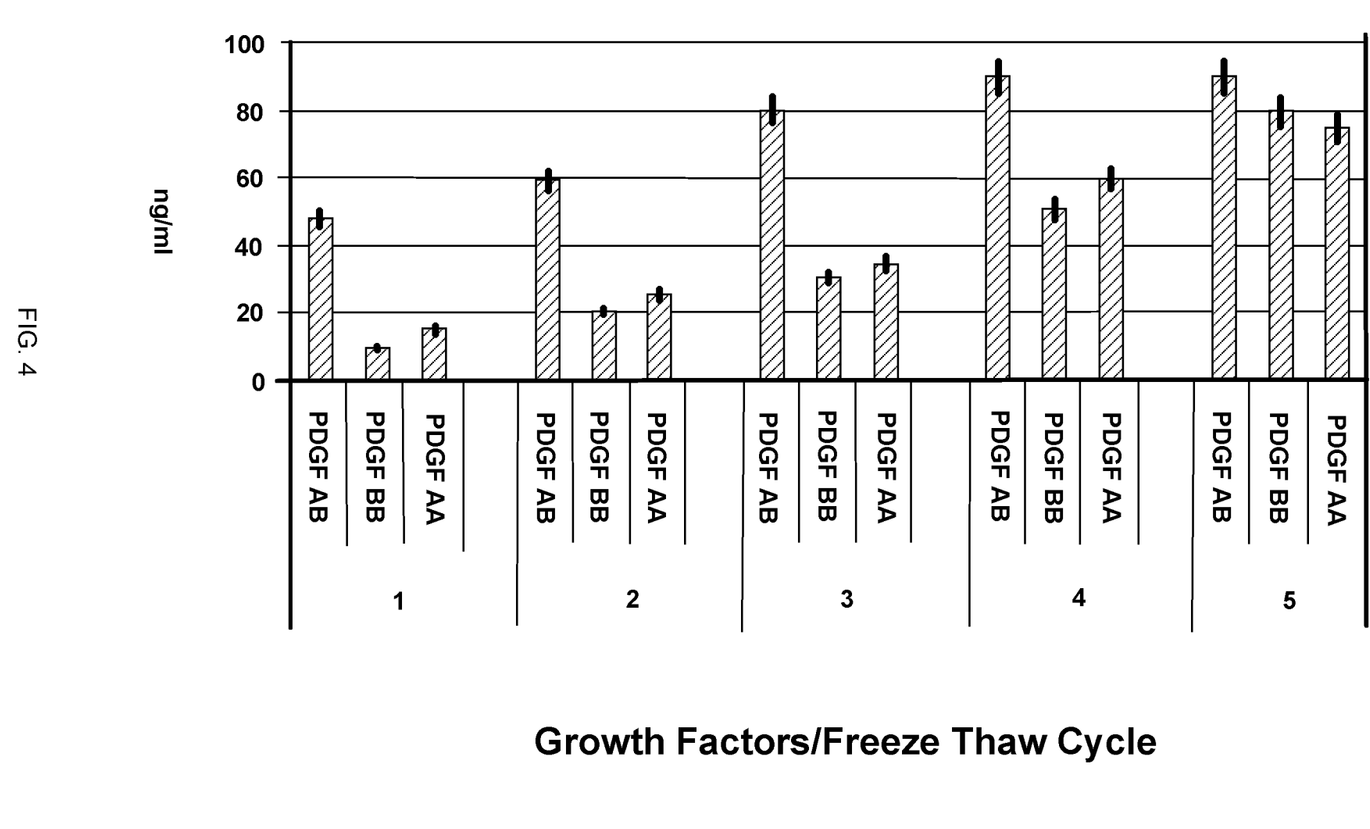
FIG. 4 schematically shows one example of specific growth factor amounts obtained after platelets were lysed over a specific number of freeze-thaw cycles.

Additionally, three specific growth factors were monitored for each of the test samples to determine the amount of each respective growth factor obtained relative to the number of freeze-thaw cycles employed. As can be seen in FIG. 4, greater number of freeze-thaw cycles not only achieved a greater number of lysed cells, but a greater amount of growth factors. Thus, the greater the number of freeze-thaw cycles employed, the greater the number of lysed platelets and the greater the amount of growth factors and other cellular constituents that can be obtained.

Example 4—Characterization of Particulate Lyophilized Platelet Lysates

Samples were prepared in triplicate in accordance with Example 1 above. Various growth factors, cytokines, and chemokines were monitored to determine which of the target cellular constituents were present in the particulate lyophilized platelet lysate and in what quantities. The results are in depicted in Table 1 below (all values are in picograms of cellular constituent per milliliter of sample (pg/ml):

TABLE 1

Effect of lyophilization and cell lysis on cellular constituents

|  | Average (pg/ml) |
| --- | --- |
| BMP-5 | 0 |
| BMP-7 | 0 |
| CD84 | 0 |
| EGF R | 113 |
| Fractalkine | 293 |
| Galectin-1 | 78 |
| IFNab R2 | 655 |
| IGFBP-1 | 165 |
| IL-10 Ra | 11 |
| IL-13 R2 | 371 |
| Insulin | 62 |
| Periostin | 1,173 |
| TNFb | 316 |
| TRANCE | 1,657 |
| WISP-1 | 1,580 |
| ACE-2 | 14,037 |
| Albumin | 14,137 |
| BMP-2 | 142 |
| IGFBP-3 | 7,881 |
| PF4 | 13,712 |

As can be seen from Table 1, the particulate lyophilized platelet lysates include a variety of different cellular constituents that can be beneficial for use in cell culture media and other applications.

Example 5—Clotting Study

Particulate lyophilized platelet lysates were prepared in accordance with Example 1 above. The particulate lyophilized platelet lysates were reconstituted in water in an amount greater than 50 wt %. The composition was added to a petri dish and monitored to determine the rate of clotting for the composition. However, no clotting was observed in the sample.

To further test the clotting activity of the particulate lyophilized platelet lysates, samples were prepared as described above and thrombin was additionally added to the composition to determine the rate of clotting. Again, no clotting was observed in the samples.

Example 6—Stem Cell Recovery Study

Particulate lyophilized platelet lysates were prepared as described in Example 1 above. The samples were stored at room temperature for 1 year. After the one year storage period, the samples were reconstituted in sterile water at a concentration of at least 50 wt %. The reconstituted particulate lyophilized platelet lysates were combined with mesenchymal stem cell cultures as a culture medium to determine the percent recovery of mesenchymal stem cells incubated with the long-term stored lysates. In three separate samples, the stem cells were recovered at 98%, 96%, and 99%, respectively, even after storage for one year at room temperature.

While the above examples are illustrative of the principles and concepts discussed herein, it will be apparent to those of ordinary skill in the art that numerous modifications in form, usage and details of implementation can be made without the exercise of inventive faculty, and without departing from those principles and concepts. Accordingly, it is not intended that the principles and concepts be limited, except as by the claims set forth below.

What is claimed is:

1. A method for preparing a particulate lyophilized platelet lysate composition for use in a cell culture medium, comprising:
    obtaining a platelet source including platelets and a fluid carrier;
    lysing the platelets to form a plurality of lysates;
    filtering the plurality of lysates after lysis to remove cellular debris, wherein the filtering is performed using a filtration membrane selected from the group consisting of polyvinylidine difluoride (PVDF), hydrophilic polytetrafluoroethylene (PTFE), regenerated cellulose (RC), polyethylene (PE), polycarbonate track etched (PCTE), polyester track etched (PETE), polyethersulfone (PES), asymmetric PES, cellulose acetate (CA), or a combination thereof;
    lyophilizing the plurality of lysates to form a particulate lyophilized platelet lysate composition having released concentrations of available growth factors, cytokines, and chemokines, wherein at least 70 wt % of the released concentrations of available growth factors, cytokines, and chemokines remain with the particulate lyophilized platelet lysate composition; and
    reconstituting the particulate lyophilized platelet lysate composition in a liquid medium to form a cell culture medium, wherein the cell culture medium does not cause clotting activity in a live cell or tissue culture.

2. The method of claim 1, wherein a concentration of lyophilized platelet lysate in the liquid medium is from about 20 wt % to about 70 wt %.

3. The method of claim 1, wherein the step of obtaining the platelet source includes concentrating platelets from platelet-containing fluid to form a platelet rich portion, and wherein the step of lysing the platelets is from the platelet rich portion.

4. The method of claim 3, wherein the step of concentrating is by centrifugation.

5. The method of claim 1, wherein the platelet source is whole blood.

6. The method of claim 1, wherein the platelet source is platelet rich plasma.

7. The method of claim 1, wherein the platelet source is from a human.

8. The method of claim 1, wherein the lysing step comprises using a freeze-thaw cycle on the platelet source.

9. The method of claim 8, wherein a single freeze-thaw cycle lyses at least 35% of platelets in the platelet source.

10. The method of claim 8, wherein freezing for the freeze-thaw cycle is performed for a period of at least 48 hours.

11. The method of claim 8, wherein the freeze-thaw cycle is repeated until a pre-determined degree of cytolysis occurs.

12. The method of claim 11, wherein freezing for each of the freeze-thaw cycles is performed for at least 24 hours.

13. The method of claim 11, wherein the pre-determined degree of cytolysis is at least 30% cytolysis by platelet count.

14. The method of claim 11, wherein at least one freeze-thaw cycle is followed by filtering the plurality of lysates to remove cell membranes and debris.

15. The method of claim 1, wherein the filtration membrane has a pore size from about 0.1 microns to 0.3 microns.

16. The method of claim 1, wherein the filtering further comprises using a pre-filter in addition to the filtration membrane.

17. The method of claim 1, wherein the lysing step comprises using sonication on the platelet source.

18. The method of claim 1, wherein 190 ng or more of released growth factors and cellular constituents including cytokines and chemokines are present per mL of lysate.

19. The method of claim 1, wherein 230 ng or more of released growth factors and cellular constituents including cytokines and chemokines are present per mL of lysate.

20. The method of claim 1, wherein at least 90 wt % of the released concentrations of available growth factors, cytokines, and chemokines remain with the particulate lyophilized platelet lysate composition.

21. A method for preparing a particulate lyophilized platelet lysate composition for use in a cell culture medium, comprising:
    obtaining a platelet source including platelets and a fluid carrier;
    lysing the platelets to form a plurality of lysates;
    filtering the plurality of lysates after lysis to remove cellular debris;
    lyophilizing the plurality of lysates by freezing the plurality of lysates in an acetone solution and drying the plurality of lysates in the acetone solution to have a water content of less than 15 wt % to form a particulate lyophilized platelet lysate composition having released concentrations of available growth factors, cytokines, and chemokines, wherein at least 70 wt % of the released concentrations of available growth factors, cytokines, and chemokines remain with the particulate lyophilized platelet lysate composition; and
    reconstituting the particulate lyophilized platelet lysate composition in a liquid medium to form a cell culture medium, wherein the cell culture medium does not cause clotting activity in a live cell or tissue culture.

22. The method of claim 21, wherein a concentration of lyophilized platelet lysate in the liquid medium is from about 20 wt % to about 70 wt %.

23. The method of claim 21, wherein the step of obtaining the platelet source includes concentrating platelets from platelet-containing fluid to form a platelet rich portion, and wherein the step of lysing the platelets is from the platelet rich portion.

24. The method of claim 21, wherein the step of concentrating is by centrifugation.

25. The method of claim 21, wherein the platelet source is whole blood.

26. The method of claim 21, wherein the platelet source is platelet rich plasma.

27. The method of claim 21, wherein the platelet source is from a human.

28. The method of claim 21, wherein the lysing step comprises using a freeze-thaw cycle on the platelet source.

29. The method of claim 28, wherein a single freeze-thaw cycle lyses at least 35% of platelets in the platelet source.

30. The method of claim 28, wherein freezing for the freeze-thaw cycle is performed for a period of at least 48 hours.

31. The method of claim 28, wherein the freeze-thaw cycle is repeated until a pre-determined degree of cytolysis occurs.

32. The method of claim 31, wherein freezing for each of the freeze-thaw cycles is performed for at least 24 hours.

33. The method of claim 31, wherein the pre-determined degree of cytolysis is at least 30% cytolysis by platelet count.

34. The method of claim 28, wherein at least one freeze-thaw cycle is followed by filtering the plurality of lysates to remove cell membranes and debris.

35. The method of claim 34, wherein filtering is performed using a filtration membrane selected from the group consisting of polyvinylidine difluoride (PVDF), hydrophilic polytetrafluoroethylene (PTFE), regenerated cellulose (RC), polyethylene (PE), polycarbonate track etched (PCTE), polyester track etched (PETE), polyethersulfone (PES), asymmetric PES, cellulose acetate (CA), and combinations thereof.

36. The method of claim 35, wherein the filtration membrane has a pore size from about 0.1 microns to 0.3 microns.

37. The method of claim 34, wherein filtering further comprises using a pre-filter in addition to the filtration membrane.

38. The method of claim 21, wherein the lysing step comprises using sonication on the platelet source.

39. The method of claim 21, wherein the lysing step comprises using filtration on the platelet source.

* * * * *